(12) United States Patent
Mirigian et al.

(10) Patent No.: US 7,338,511 B2
(45) Date of Patent: Mar. 4, 2008

(54) SOLID EMBOLIC MATERIAL WITH VARIABLE EXPANSION

(75) Inventors: Gregory E. Mirigian, Dublin, CA (US); Huey Quoc Chan, San Jose, CA (US); Thomas Yung-Hui Chien, San Jose, CA (US); Stephen C. Porter, Fremont, CA (US); Robert P. Eury, Cupertino, CA (US)

(73) Assignee: Boston Scientific-Scimed, Inc., Maple Grove, MN (US)

( * ) Notice: Subject to any disclaimer, the term of this patent is extended or adjusted under 35 U.S.C. 154(b) by 766 days.

(21) Appl. No.: 10/155,563

(22) Filed: May 24, 2002

(65) Prior Publication Data

US 2003/0220666 A1 Nov. 27, 2003

(51) Int. Cl.
*A61M 29/00* (2006.01)
(52) U.S. Cl. ...................................................... 606/200
(58) Field of Classification Search ................ 606/200, 606/194; 424/426
See application file for complete search history.

(56) References Cited

U.S. PATENT DOCUMENTS

| | | | |
|---|---|---|---|
| 4,311,146 A | 1/1982 | Wonder | |
| 4,341,218 A | 7/1982 | U | |
| 4,364,392 A | 12/1982 | Strother et al. | |
| 4,395,806 A | 8/1983 | Wonder et al. | |
| 4,471,779 A | 9/1984 | Antoshkiw et al. | |
| 4,545,367 A | 10/1985 | Tucci | |
| 4,751,924 A | 6/1988 | Hammerschmidt et al. | |
| 4,819,637 A | 4/1989 | Dormandy, Jr. et al. | |
| 5,002,556 A | 3/1991 | Ishida et al. | |
| 5,222,970 A | 6/1993 | Reeves | |
| 5,634,936 A * | 6/1997 | Linden et al. | 606/213 |
| 5,747,591 A | 5/1998 | Chen et al. | |
| 5,830,178 A * | 11/1998 | Jones et al. | 604/507 |
| 5,913,871 A | 6/1999 | Werneth et al. | |
| 5,919,163 A | 7/1999 | Glickman | |
| 6,056,906 A | 5/2000 | Werneth et al. | |
| 6,152,144 A | 11/2000 | Lesh et al. | |
| 6,152,943 A | 11/2000 | Sawhney | |
| 6,165,193 A | 12/2000 | Greene, Jr. et al. | |
| 6,293,960 B1 | 9/2001 | Ken | |
| 6,306,144 B1 | 10/2001 | Sydney et al. | |
| 6,387,391 B1 * | 5/2002 | Shikinami et al. | 424/426 |
| 6,506,194 B1 * | 1/2003 | Hajianpour | 606/95 |
| 6,511,468 B1 * | 1/2003 | Cragg et al. | 604/508 |
| 6,551,334 B2 * | 4/2003 | Blatter et al. | 606/153 |
| 6,558,367 B1 * | 5/2003 | Cragg et al. | 604/523 |
| 6,855,153 B2 * | 2/2005 | Saadat | 606/194 |

FOREIGN PATENT DOCUMENTS

| | | |
|---|---|---|
| DE | 4028466 A1 | 3/1992 |
| WO | WO 99/03404 | 1/1999 |
| WO | WO 01/15608 A1 | 3/2001 |

* cited by examiner

*Primary Examiner*—Anhtuan T. Nguyen
*Assistant Examiner*—Tuan V. Nguyen
(74) *Attorney, Agent, or Firm*—Vista IP Law Group, LLP

(57) ABSTRACT

A solid embolic material that is capable of filling irregularly shaped and asymmetrical vascular defects in a controlled and predictable manner, without the difficulties associated with delivery of the embolic material through a microcatheter and containment of the embolic material in a defect. A detachable embolic balloon with optional check valve for maintaining liquid in the balloon prior to curing and optional multi-leaflet covering to prevent the balloon from expanding into the native vascular lumen.

7 Claims, 4 Drawing Sheets

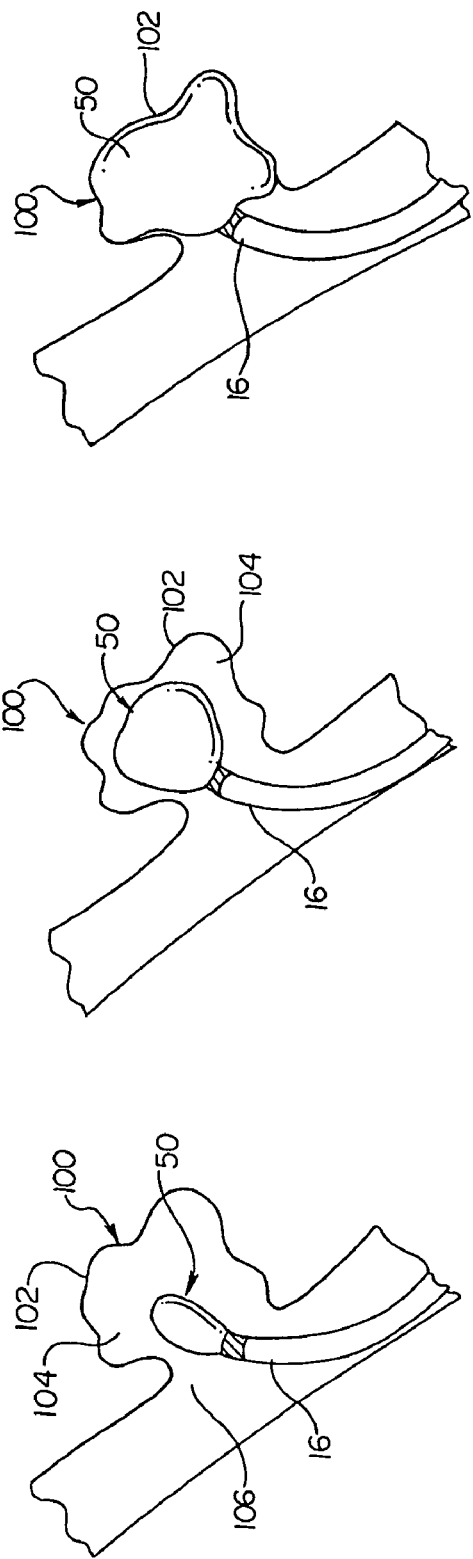

SOLID EMBOLIC MATERIAL WITH VARIABLE EXPANSION

FIELD OF THE INVENTION

The present invention generally pertains to embolic balloons and delivery systems. In particular, the present invention relates to embolic balloons delivered by intravascular microcatheters to vascular defects.

BACKGROUND OF THE INVENTION

In treating vascular defects such as aneurysms and fistulas, which commonly occur in the neurovasculature, a microcatheter is navigated through the patient's vasculature until a distal end of the microcatheter is adjacent the defect. An embolic material is then delivered through the microcatheter and into the vascular defect, to thereby fill and seal-off the defect. However, because vascular defects like aneurysms and fistulas often have irregularly shaped and asymmetrical volumes, it is difficult to accurately and completely fill the defect with embolic coils, balloons or other embolic devices, which are typically symmetrically shaped. Although liquid embolic materials tend to fill irregularly shaped and asymmetrical volumes more precisely and completely, liquid embolic materials are often difficult to deliver through a microcatheter and are often difficult to contain within the defect. Accordingly, there is a substantial need for an embolic material and delivery system that is capable of filling an asymmetrical and irregularly shaped vascular defect, that is easy to deliver with a microcatheter, and that is easy to contain within the defect.

There is also an ongoing need for improved embolic balloons and associated delivery systems. In particular, there is a need for detachable embolic balloons that may be easily delivered and maintained in the vascular defect so as to not protrude into the native vascular lumen.

SUMMARY OF THE INVENTION

To address this substantial unmet need, the present invention provides, in an exemplary non-limiting embodiment, a solid embolic material that is capable of filling irregularly shaped and asymmetrical vascular defects in a controlled and predictable manner, without the difficulties associated with delivery of embolic material through a microcatheter and containment of embolic material in a defect. The solid embolic material of the present invention may be inflated with a liquid (e.g., liquid embolic material) to further engage the internal walls of the defect and to more completely fill the irregularly shaped volume of the defect.

The present invention also provides, in another exemplary non-limiting embodiment, a detachable embolic balloon and associated delivery system. The detachable embolic balloon in this embodiment may be filled with a curable liquid wherein the curing process may be aided by thermal means. The detachable embolic balloon may optionally incorporate a check valve for maintaining the liquid in the balloon prior to curing and/or a multi-leaflet covering to prevent the balloon from expanding into the native or parent vascular lumen.

BRIEF DESCRIPTION OF THE DRAWINGS

FIGS. 3A-3C schematically illustrate the delivery of the solid embolic material into an aneurysm having an irregular shape;

DETAILED DESCRIPTION

Figure 1:
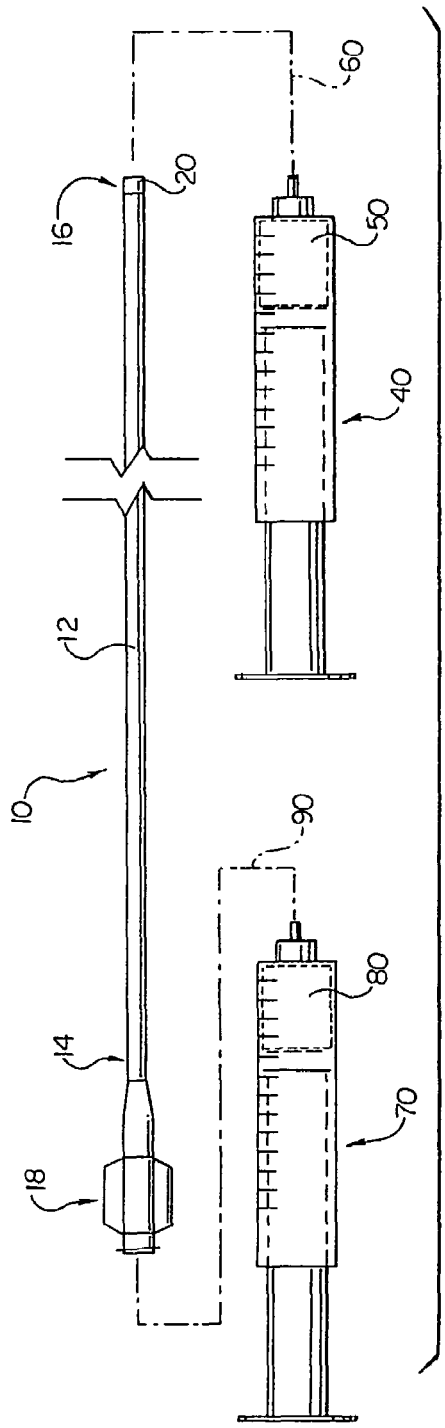
FIG. 1 illustrates a microcatheter, a syringe containing a solid embolic material therein for placement into a distal end of the microcatheter, and a syringe containing a fluid for injection into a proximal end of the catheter.

The following description should be read with reference to the drawings wherein like reference numerals indicate like elements throughout the several views. The detailed description and drawings illustrate embodiments by way of example, not limitation.

Refer now to FIG. 1 which illustrates a microcatheter 10, a syringe 40, and a syringe 70. Syringe 40 contains a solid embolic material 50 which may be disposed or injected into the catheter 10 as indicated by arrow 60. Syringe 70 contains a fluid 80 (e.g., radiopaque saline solution or liquid embolic agent) for injection into the catheter 10 as indicated by arrow 90.

Microcatheter 10 may be used to deliver the solid embolic material 50 to a vascular defect such as an aneurysm or fistula having an internal wall defining an internal volume therein. The solid embolic material 50 is particularly suitable for filling internal volumes that are irregular in shape and eccentric relative to the neck or opening to the native vascular lumen.

Intravascular catheter 10 is sized (length and diameter) and designed (pushability and trackability) to navigate a patient's vascular system to access vascular defects in the neurovasculature, coronary vasculature and/or peripheral vasculature. Intravascular catheter 10 may include one or more lumens and may be designed to accommodate a guide wire (not shown) and/or to incorporate a distally disposed inflatable balloon (not shown). Although a single lumen intravascular microcatheter 10 is illustrated, those skilled in the art will recognize that a wide variety of intravascular catheters may be used to deliver solid embolic material 50 to a vascular defect.

The basic design and construction of microcatheter 10 is conventional in the art, and is provided by way of example, not limitation. Intravascular microcatheter 10 includes an elongate shaft 12 having proximal end 14 and a distal end 16. A hub assembly 18 is connected to the proximal end 14 of the elongate shaft 12. A lumen (not visible) extends through the hub assembly 18 and through the length of the shaft 12 to a distal-facing opening (not visible) in the distal end 16 of the shaft 12. Hub assembly 18 facilitates connection to ancillary devices such as syringe 70 for the injection or infusion of fluids 80 such as contrast media (e.g., radiopaque dye and saline solution) and liquid embolic agents (e.g., cyanoacrylate) into the lumen and out the opening at the distal end 16. The distal end 16 may be rendered radiopaque by utilizing radiopaque loading in the polymers of the distal end 16 of the shaft 12 or by utilizing a radiopaque marker band 20 disposed thereon. Rendering the distal end 16 radiopaque allows the tip to be precisely navigated utilizing x-ray radiographic techniques.

Solid embolic material 50 defines an initially solid volume when disposed in syringe 40 and when disposed in the lumen at the distal end 16 of the shaft 12. Sufficient solid embolic material is disposed in the lumen of the catheter 10 to fill the internal volume or lining of the targeted vascular defect. Solid embolic material 50 is readily stretchable, viscid and self-sealing such that the material is able to expand upon injection of a fluid into the solid volume thereof. Upon injection of a fluid into the solid volume, the solid embolic material 50 expands to create an internal volume which self-seals and retains the fluid therein. Upon expansion, the solid embolic material 50 is not elastically biased to its original state, but rather tends to assume and hold its expanded state with little or no pressure maintained in the volume created therein. To this end, the solid embolic material 50 is much like bubble-gum in its behavior, albeit for substantially different applications requiring substantially different compositions and designs.

The fluid 80 used to inflate the solid embolic material 50 may comprise a radiopaque liquid or a liquid embolic material (e.g., cyanoacrylate), for example. The solid embolic material 50 facilitates containment of the liquid embolic material in the vascular defect, and the liquid embolic material may be selected to solidify after injection into the solid embolic material 50, in order to assist in sealing the inflated internal volume of the solid embolic material 50. To facilitate injection of fluid 80 into the solid embolic material, a pressurized fluid source such as a syringe 70 may be connected to the hub assembly 18 of the catheter 10. Such a device 70 may also be used to pressurize the lumen in the catheter 10 to urge the solid embolic material 50 out of the distal end 16 of the catheter 10 and into the vascular defect.

The solid embolic material 50 preferably has relatively high cohesivity and simultaneously is in a state capable of plastic deformation at low pressures. In addition, the solid embolic material 50 preferably has little or no elastic restoring force that will cause the material 50 to contract after pressure is released subsequent to inflation within the defect 100. Further, in order to facilitate delivery in a compact size and subsequent inflation to a relatively large size, the solid embolic material 50 will preferably withstand 1000% elongation or more, for example, during inflation. Polymer based materials are probably the best candidates for this application. However there are a number of material classes that might be used, and within each class, there are a large number of possible formulations that may have suitable properties. Accordingly, although specific examples are given, the examples are illustrative only.

In one embodiment, for example, the solid embolic material 50 may comprise a medium to high molecular weight polymer in a semi-swollen or highly plasticized state. An example of such a polymer comprises poly(vinyl acetate) dissolved in ethanol/ethyl lactate. Another example of such a polymer comprises alkyl methacrylate (the alkyl side-chain being greater than C4) dissolved in a plasticizer (e.g., fatty acid ester, di-alkyl citrate, or triglyceride). Many other combinations of polymers with molecular weights greater than 100 KDa and blended with solvents and/or plasticizers may be applicable in this embodiment as well. The types and concentrations of the polymer/solvent mixture may be selected to optimize the desired characteristics. As an alternative, one of the components of the polymer solution/mixture may melt at a temperature slightly above body temperature and act as a plasticizer for the other component. In this alternative embodiment, a localized heat source may be used to heat the first component to a temperature above body temperature (37C).

Other embodiments of polymers suitable for the solid embolic material 50 include polymers that can be transformed to a low modulus state in-situ by small localized temperature changes. Examples of such polymers include non-cross linked polymers having semi-crystalline and amorphous phases (or possessing discrete liquid-crystalline phases) which have first or second order thermal transitions slightly above maximum body temperature (42C), such as long hydrocarbon side-chain acrylic copolymers. Such a polymer may utilize localized heating preferably during inflation and may incorporate tissue adhesive properties when heated.

Other examples of polymers that can be transformed to a low modulus state in situ by small localized environment (e.g. temperature) changes include high molecular weight linear polymers, copolymers or blends in a swollen gel or dissolved state which have a sharp decrease in solubility/swelling within the incorporated solvent in response to changes in temperature, ionic strength, or pH, such as poly(n-isopropyl acrylamide) copolymer/blend hyrogels. Such polymers may utilize localized cooling during inflation which causes the polymer to change from a solid or dense gel at body temperature to a swollen or loose hydrogel material capable of deformation at lower temperatures.

If a mixture of a polymer and a solvent is used, it may be important to ensure that the polymer remains mixed with the solvent until the time of use, in order for the solid embolic material 50 to retain its desired characteristics. For example, the polymer and solvent may be kept in separate containers and manually mixed just prior to use, using a syringe 40 to inject the mixture into the distal end 16 of the catheter 10 as shown in FIG. 1.

Figure 2B:
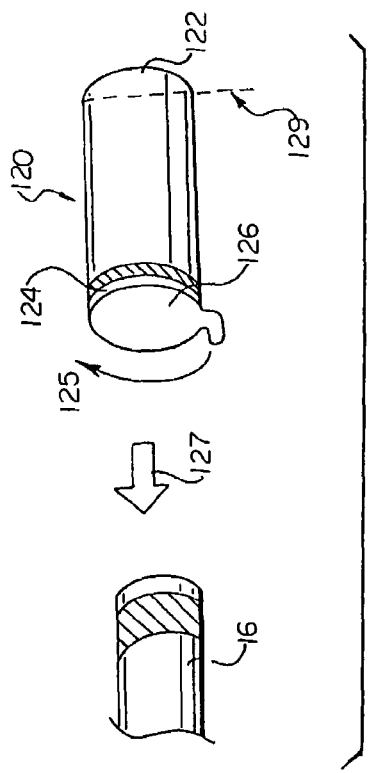
FIGS. 2A and 2B illustrate alternative methods of containing the solid embolic material, and loading the solid embolic material into the distal end of the microcatheter.
Figure 2A:
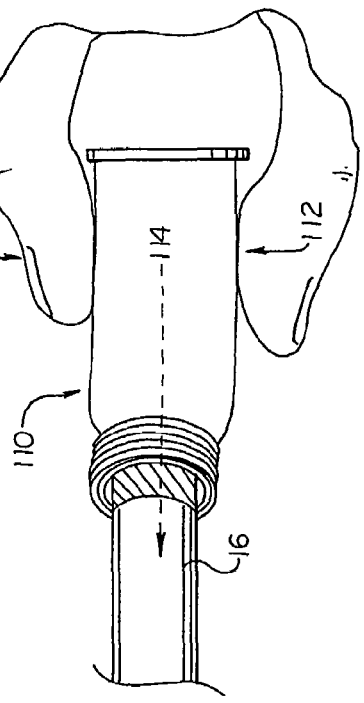

Alternatively, a container 110 may contain a pre-mix of the polymer/solvent which may then be directly injected into the distal end 16 of the catheter 10 as shown in FIG. 2A. In this particular embodiment, the container 110 may be rolled, squeezed or shaken to ensure a homogenous mix, opened by removal of a cap (not shown), placed over the distal end 16 of the catheter 10, and manually squeezed (as indicated by arrows 112) to inject the mixture therein (as indicated by arrow 114).

As a further alternative, a short tubular container 120 containing a premix of the polymer/solvent may be attached to the distal end 16 of the catheter 10 as shown in FIG. 2B. In this particular embodiment, the container 120 has a sealed distal end 122 that may be cut to provide an opening, and a proximal end 124 sealed by cover 126. The proximal end 124 is sized to snuggly fit over and attach to the distal end 16 of the catheter 10. The container 120 may be rolled, squeezed or shaken to ensure a homogenous mix, opened by removal of the cover 126 (as indicated by arrow 125), attached to the distal end 16 of the catheter 10 by sliding the proximal end 124 thereon (as indicated by arrow 127), and the distal end 122 cut (as indicated by arrow and dashed line 129) to provide a distal opening.

With reference to FIGS. 3A-3C, the solid embolic material 50 may be used to treat a vascular defect 100 such as an aneurysm or fistula. The vascular defect 100 includes an internal wall 102 defining an internal volume 104. Although described herein with reference to the treatment of a vascular defect 100, the solid embolic material 50 may also be used to occlude vessels for therapeutic purposes.

After preparing the catheter 10 with the solid embolic material 50 disposed in the distal end 16 thereof as described above, the catheter 10 may be navigated through a patient's vascular system until the distal end 16 is disposed adjacent the opening 106 to the vascular defect 100 as seen in FIG. 3A.

The solid embolic material 50 may then be urged from the lumen at the distal end 16 of the catheter 10 and into the vascular defect 100 as seen in FIG. 3B. This may be accomplished by applying fluid pressure in the catheter lumen proximal of the solid embolic material 50 using syringe 70 connected to the hub assembly 18.

The solid embolic material 50 may then be further urged into the vascular defect until the solid embolic material substantially conforms to the internal wall 102 and substantially fills the internal volume 104 as seen in FIG. 3C, despite the irregular shape of the wall 102 and volume 104. This may be accomplished by applying more fluid pressure in the catheter lumen proximal of the solid embolic material 50 using syringe 70 connected to the hub assembly 18, to cause the fluid 80 to be injected into the solid embolic material 50 and to inflate the same. The solid embolic material 50 may be inflated to varying degrees to conform to vascular defects 100 of varying size and shape.

After the defect 100 is substantially filled as confirmed by x-ray fluoroscopy, the solid embolic material 50 in the defect 100 may be detached from the distal end 16 of the catheter 10 (and any solid embolic material 50 remaining in the distal end 16) by rotating the catheter 10 and/or by pulling the catheter 10 proximally.

Refer now to FIGS. 4A-4D which schematically illustrate a distal portion of a detachable embolic balloon catheter 200. With specific reference to FIG. 4A, catheter 200 includes an elongate shaft 212 having a proximal end (not visible) and a distal end. Catheter 200 also includes a detachable balloon 214 having a proximal end thereof releasably connected to the distal end of the shaft 212. The detachable balloon 214 may comprise, for example, any of the materials discussed previously with reference to solid embolic material 50.

The shaft 212 may include a guide wire lumen lateral attachment 216 which defines a guide wire lumen (not visible) extending therethrough to slidably accommodate conventional guide wire 400. The side attachment 216 may comprise, for example, a short tube connected to the shaft 212 by adhesive, thermal bond, and/or a heat shrink sleeve. The shaft 212 may also include a radiopaque marker band 218 connected to its distal end. Radiopaque marker band 218 may comprise, for example, a band of dense metal such as platinum, gold, iridium, or an alloy thereof.

Figure 4A:
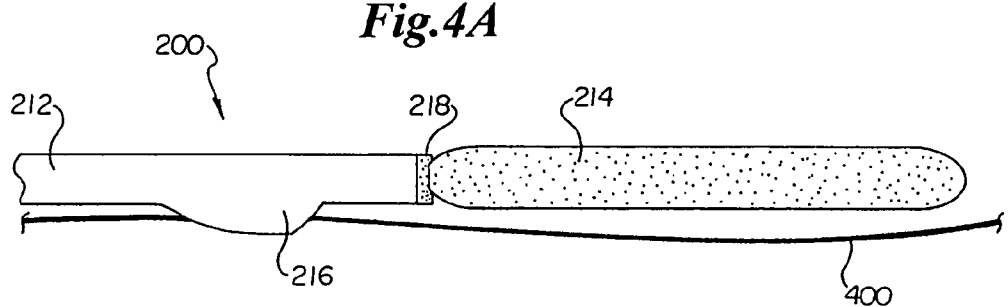
FIGS. 4A-4D schematically illustrate a first embodiment of a detachable embolic balloon and delivery system.
Figure 4B:
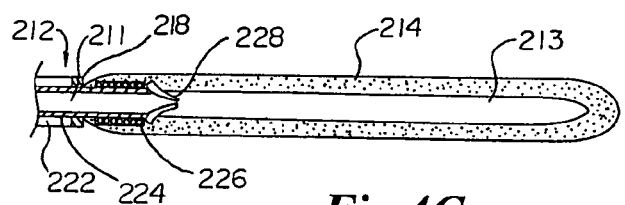

With reference to FIG. 4B, the elongate shaft may comprise an outer tubular layer 222 surrounding an inner tubular layer 224 which extends distally beyond the outer layer 222. A reinforcement layer (not shown) such as a metallic or polymeric coil or braid may be disposed between the inner layer 224 and the outer layer 22 to enhance navigational performance of the shaft 212. The marker band 218 may be disposed on the inner layer 224 distal of the outer layer 22 such that the outside diameter of the marker band 218 is flush with or does not exceed the outside diameter of the outer layer 222.

The proximal end of the balloon may include a radiopaque marker coil 226 molded into the wall of the proximal end of the balloon 214 or connected thereto by other means (e.g., adhesive, thermal bonding, etc.) The radiopaque marker 226 may comprise, for example, a wound wire coil of a dense metal such as platinum, gold, iridium, or an alloy thereof. Together with radiopaque marker band 218, radiopaque marker coil 226 facilitates radiographic visualization during deployment of the detachable balloon 214.

The inner tubular layer 224 defines a lumen 211 which extends through the full length of the shaft 212 and is in fluid communication with the interior 213 of the balloon 214 via optional check valve 228. Check valve 228 may comprise a duck-bill type or flapper type valve that permits fluid flow in only the distal direction. As will be described in more detail hereinafter, check valve 228 helps retain the inflation liquid in the interior 213 of the balloon 214 to allow the inflation liquid to cure or to otherwise permit detachment of the balloon 214 from the distal end of the shaft 212 after filling the balloon 214 with a liquid. Detachment of the balloon 214 from the distal end of the shaft 212 may be accomplished with an electrolytic detachment system or with a break-away bond as described in more detail below.

Because, the balloon 214 may comprise a material that is highly compliant and flexible at low inflation pressures to permit low pressure expansion (e.g., less than 2 ATM), the connection between the distal end of the shaft 212 and the proximal end of the balloon 214 does not necessarily need to withstand high inflation pressures (e.g., greater than 15 ATM). Thus, the connection between the distal end of the shaft 212 and the proximal end of the balloon 214 may be made detachable by a weak chemical and/or mechanical bond, for example, that may be broken upon the application of torsional and/or longitudinal forces. For example, after the balloon 214 has been deployed, twisting and pulling the proximal end of the shaft 212 may be utilized as a means to break the bond and detach the balloon 214 from the shaft 212. A relatively weak bond may be provided, for example, by utilizing a relatively lubricious polymer (e.g., PTFE or HDPE without surface activation) for the inner tubular layer 224 and a conventional biocompatible adhesive such as cyanoacrylate to bond the inner tube 224 to the proximal end of the balloon 214.

Figure 4C:
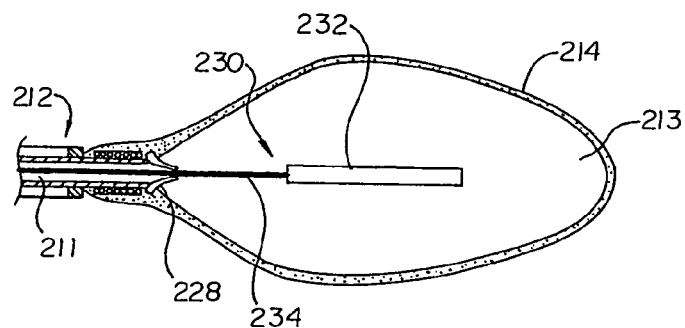
Figure 4D:
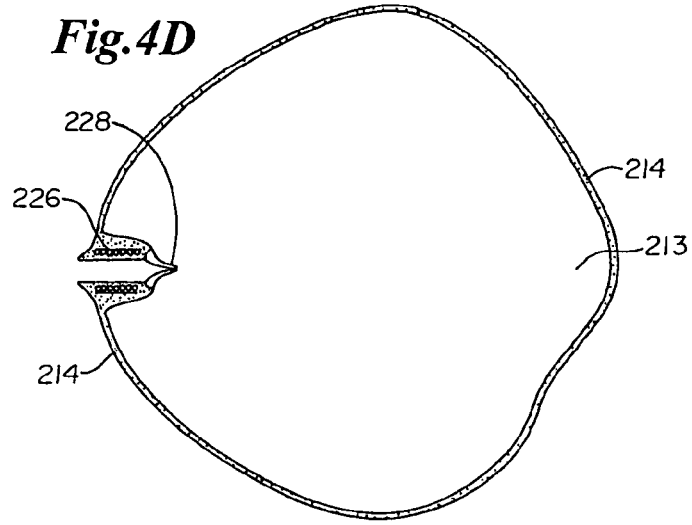

As mentioned above, the interior 213 of the balloon 214 may be inflated or otherwise filled with a curable liquid such as acrylic monomers, urethane prepolymers, epoxy resins, cyanoacrylates, silicones, or similar material. The polymerization or curing process of such materials or a thermal transition of such materials may be accelerated or induced by heat. Accordingly, a heating device 230 may be introduced through the lumen 211 of the shaft 212 and into the interior 213 of the balloon 214 to supply thermal energy to the curable liquid disposed in the interior 213 of the balloon 214 as shown in FIG. 4C. The heating device 230 may also be used to heat the balloon 214 if the balloon 214 is formed of a thermally responsive material. The heating device 230 may comprise, for example, a hollow guide wire type shaft 234 having a distally disposed heating element 232. By way of example, not limitation, the heating element 232 may comprise an electrical resistive heating coil powered via leads (not shown) extending through the shaft 234 to a power source (not shown).

Alternatively, the polymerization or curing process may be induced or accelerated by contact with an initiating chemical component or catalyst which may be present within the balloon 214 as a coating on the inside surface of the balloon 214 or as a blend contained in the balloon material. Alternatively, the initiating chemical component or catalyst may be delivered into the balloon 214 via a separate lumen in the shaft 212 or via a separate tube (e.g. hypotube) advanced through the shaft 212.

In use, the catheter 200 is navigated through the patient's vascular system utilizing radiographic visualization or other visualization techniques until the balloon 214 is disposed adjacent the vascular defect. The balloon 214 is then advanced or otherwise urged into the vascular defect. The interior 213 of the balloon 214 is then inflated with a curable liquid via lumen 211 of the shaft 212. As the balloon 214 is being inflated, the check valve 228 permits the liquid to enter the interior 213 of the balloon 214 but prevents substantial egress of the liquid thereout. The balloon 214 may then be inflated until the perimeter of the balloon 214 substantially conforms to the contours of the defect. After inflation of the balloon 214, the liquid in the balloon is allowed to cure, with or without the use of a catalyst or an accelerator. If desired, after or during inflation of the balloon 214, a heating device 230 may be advanced into the interior 213 of the balloon 214 and activated to initiate and/or accelerate the solidification process of the curable liquid, or to heat the balloon material. Once the inflation liquid has cured or otherwise substantially solidified, the catheter shaft 212 may be released from the balloon 214 by an externally activated detachment mechanism or by twisting and pulling, for example, thus leaving the detachable balloon 214 and associated components 226/228 in the vascular defect.

Figure 5A:
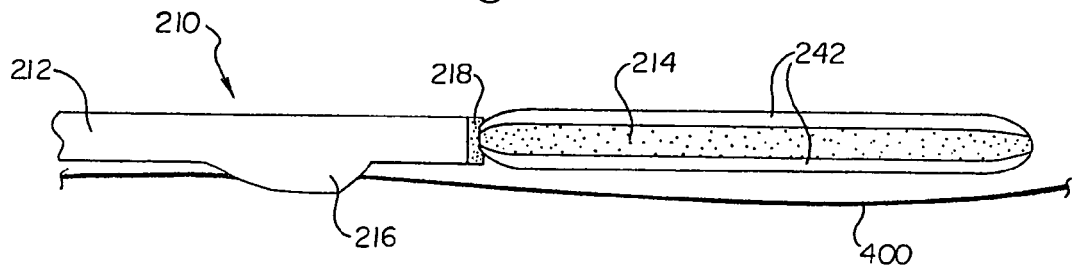
FIGS. 5A-5D schematically illustrate a second embodiment of a detachable embolic balloon and delivery system.
Figure 5B:
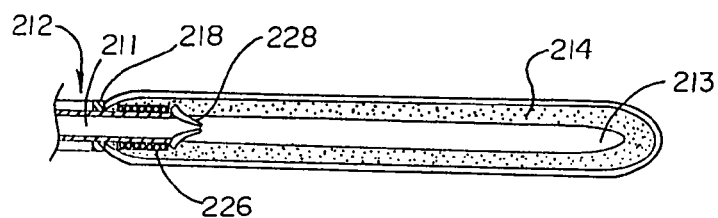

Refer now to FIGS. 5A-5D which schematically illustrate a distal portion of a detachable embolic balloon catheter 210, which is substantially the same in design and function as catheter 200 except as described herein and illustrated in the drawings. As seen in FIGS. 5A and 5B, a plurality of leaflets 242 (e.g., 2, 3, 4, or more) are uniformly disposed about the balloon 214 and extend along the balloon 214 to a distal apex thereof. The proximal ends of the leaflets 242 may be hinged and are attached to the proximal end of the balloon 214. The distal ends of the leaflets 242 collectively meet adjacent the distal apex of the balloon 214. The leaflets 242 may be formed of a flexible polymeric or metallic material which is generally more rigid than the material of the balloon 214. The leaflets 242 may have a rectangular cross-section with a convex exterior surface, a concave interior surface, and a distal inward taper to conform to the profile of the balloon 214.

Figure 5C:
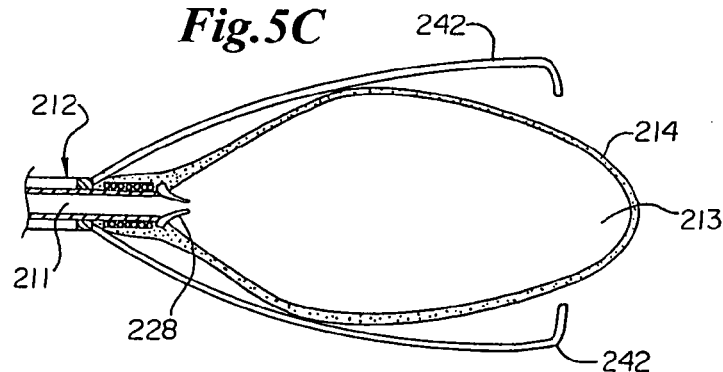
Figure 5D:
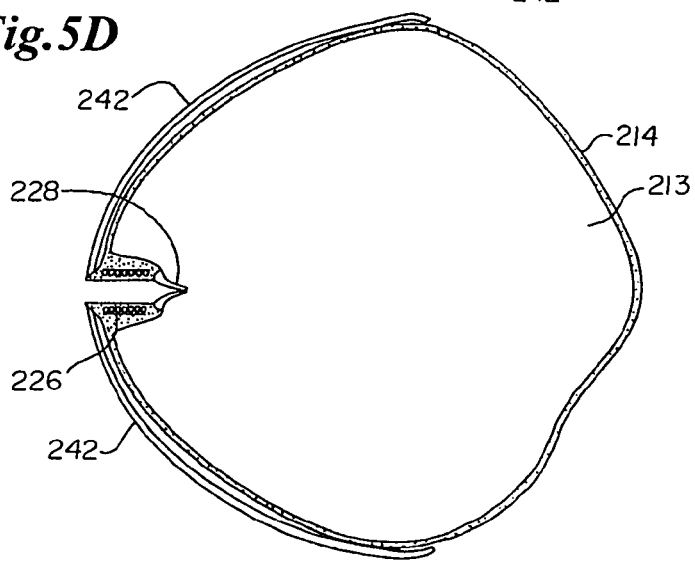

After the balloon 214 has been disposed in the vascular defect as described previously, and as the balloon 214 is being inflated, the leaflets 242 separate and expand about hinge points at their respective proximal ends as shown in FIG. 5C. Upon further expansion, the leaflets 242 and the balloon 214 conform to the inside surface of the defect as shown in FIG. 5D. Because the leaflets 242 are relatively more rigid than the balloon 214, and because the leaflets 242 extend across the opening to the vascular defect, the leaflets 242 prevent the balloon 214 from expanding into the native vascular lumen to thereby confine the balloon 214 within the interior of the vascular defect. The use of catheter 210 is otherwise the same as catheter 200 described previously.

It should be understood that this disclosure is, in many respects, only illustrative. Changes may be made in details, particularly in matters of shape, size, arrangement of parts and order of steps without departing from the scope of the invention. The invention's scope is, of course, defined in the language in which the appended claims are expressed.

What is claimed is:

1. An embolic device comprising a solid material defining an initially solid volume which is viscid and self-sealing such that the material is able to retain a fluid injected into the solid volume at an injection pressure, said solid material being extensible, substantially inelastic and capable of expanding in volume to an expanded state upon injection of said fluid into said solid material and substantially maintaining said expanded state against a force exerted by a wall of a tissue cavity without said injection pressure maintained by said injected fluid, wherein said solid material facilitates containment of a liquid embolic material placed in the embolic device.

2. An embolic device as in claim 1, wherein the fluid comprises radiopaque liquid.

3. An embolic device as in claim 1, wherein the fluid comprises a liquid embolic material.

4. An embolic device as in claim 1, wherein the material comprises a pre-polymer.

5. An embolic device as in claim 1, wherein the material comprises polymer.

6. An embolic device as in claim 1, wherein the material comprises a polymer and a solvent mixture.

7. An embolic system, comprising:

an elongate catheter having a proximal end, a distal end and a lumen extending therethrough; and a solid embolic material disposed in the lumen at the distal end of the catheter, the solid embolic material comprising a solid material defining an initially solid volume which is viscid and self sealing such that the material is able to retain a fluid injected into the solid volume at an injection pressure, said solid material being extensible, substantially inelastic and capable of expanding in volume to an expanded state upon injection of said fluid into said solid material and substantially maintaining said expanded state against a force exerted by a wall of a tissue cavity without said injection pressure maintained by said injected fluid, wherein said solid material facilitates containment of a liquid embolic material placed in the embolic device.

* * * * *